(12) United States Patent
Eade

(10) Patent No.: US 12,295,922 B2
(45) Date of Patent: May 13, 2025

(54) TOPICAL MEDICAMENT FOR USE IN TREATMENT OF ANORECTAL INFLAMMATION

(71) Applicant: Kenneth Eade, Monaco (MC)

(72) Inventor: Kenneth Eade, Monaco (MC)

( * ) Notice: Subject to any disclaimer, the term of this patent is extended or adjusted under 35 U.S.C. 154(b) by 0 days.

(21) Appl. No.: 17/990,777

(22) Filed: Nov. 21, 2022

(65) Prior Publication Data

US 2024/0165053 A1    May 23, 2024

(51) Int. Cl.
| | | |
|---|---|---|
| *A61K 31/137* | (2006.01) | |
| *A61K 9/00* | (2006.01) | |
| *A61K 9/06* | (2006.01) | |
| *A61K 47/06* | (2006.01) | |
| *A61K 47/22* | (2006.01) | |
| *A61K 47/26* | (2006.01) | |

(52) U.S. Cl.
CPC .......... *A61K 31/137* (2013.01); *A61K 9/0014* (2013.01); *A61K 9/06* (2013.01); *A61K 47/06* (2013.01); *A61K 47/22* (2013.01); *A61K 47/26* (2013.01)

(58) Field of Classification Search
CPC ...... A61K 31/137; A61K 9/0014; A61K 9/06; A61K 47/06

See application file for complete search history.

(56) References Cited

U.S. PATENT DOCUMENTS

| | | | | |
|---|---|---|---|---|
| 4,906,239 A | * | 3/1990 | Bruhl .................... | A61M 31/00 604/104 |
| 4,938,221 A | * | 7/1990 | Tuffel .................... | A61F 7/123 607/113 |
| 5,004,636 A | * | 4/1991 | Parris ........................ | B32B 7/04 514/882 |
| 5,962,008 A | * | 10/1999 | Carroll ................... | A61K 31/60 514/882 |
| 6,391,869 B1 | * | 5/2002 | Parks ..................... | A61K 45/06 514/252.19 |
| 2022/0249512 A1 | * | 8/2022 | Slagel ...................... | A61K 9/06 |

* cited by examiner

Primary Examiner — Sikarl A Witherspoon

(57) ABSTRACT

A medicament for use in the treatment of anorectal inflammation in hemorrhoids contains a petroleum base, water, phenylephrine hydrochloride, tocopherol acetate, and micronized sucrose.

7 Claims, No Drawings

TOPICAL MEDICAMENT FOR USE IN TREATMENT OF ANORECTAL INFLAMMATION

BACKGROUND OF THE INVENTION

1. Field of the Invention

The present invention pertains to the field of topical ointments or creams that may be used to soothe pain, swelling, and itching associated with anorectal inflammation caused by hemorrhoids. More specifically, the topical ointment contains a vasoconstrictor in combination with an antibacterial agent.

2. Statement of the Problem

Discomfort due to anorectal inflammation includes pain and itching in tissues proximate to the rectum. Anorectal inflammation is most often found in irritated hemorrhoidal tissues, i.e., hemorrhoids, which are varicose dilations of veins in the superior or inferior hemorrhoidal plexus. The dilation results from a persistent increase in venous pressure. Inflammation of anorectal tissues is a complicating factor that enhances the severity of hemorrhoids.

Hemorrhoids are among the most frequent proctological conditions at a general practitioner practice. Their incidence in the general population ranges between 4.4% and 36.4%. Hemorrhoids are vascular cushions that close the anal canal and empty during defecation, allowing stool passage. These formations are adhered to the anal wall through fibrous ligaments.

When these fibrous attachments degenerate, hemorrhoids may prolapse out of the anal canal, engorge, and bleed. There are many different categories of hemorrhoids or hemorrhoidal conditions, and some of these are medically severe conditions requiring surgery. External prolapsed hemorrhoids are classified by their location as internal or external. Prolapsed internal hemorrhoids are always covered by intestinal mucosa. On the other hand, external hemorrhoids originate below the dentate line and are covered by skin. Acute prolapse of internal hemorrhoids, due to obstruction of venous return and stasis, is presented with edema, inflammation, and acute pain. The aforementioned symptoms can be very incapacitating for several weeks if untreated, and conservative management is opted.

Mucotaneous hemorrhoids result from a varicose dilation of a vein connecting the superior and inferior hemorrhoidal plexuses with the formation of internal and external hemorrhoids in continuity. Prolapsed hemorrhoids are internal hemorrhoids that have descended below the pectinate line with protrusion outside the anal sphincter. Strangulated hemorrhoids are prolapsed hemorrhoids that are sufficiently severe for the action of the anal sphincter to have occluded the blood supply. Thrombosed hemorrhoids contain clotted blood.

The patient often suffers from chronic pain and itching. The inflamed tissue becomes sensitized to the application of medicines intended to treat the problem, and this sensitization can actually cause the medicines to worsen the problem that they are intended to treat. Over time, surgery may be required to remove hemorrhoidal tissues; however, even surgery sometimes does not eliminate the continuing tendency of these tissues to become inflamed. In fact, surgery is only a temporary solution to the problem in most instances. Thus, the cycle of inflammation, discomfort, and sensitization repeats itself even after surgery.

Surgical ligation of hemorrhoids is complicated by the risk of infection, and exotic procedures have been developed, e.g., as described in U.S. Pat. No. 4,621,635, which teaches rubber band ligation of internal hemorrhoidal tissue, followed by a laser incision around the perimeter of the base of the external hemorrhoid portions. The surface of the external hemorrhoid is then evaporated with a traversing movement of the laser beam. The laser beam is then employed to form a cavity into the core of the hemorrhoid and dimensioned to accommodate the subsequent insertion of a cryogenic probe. The probe freezes the hemorrhoidal tissue from the interior outwardly.

The majority of hemorrhoidal conditions are not so severe as to require surgery. Hemorrhoids and associated discomfort due to anorectal inflammation can be treated through the use of topical ointments. Most recent U.S. patents directed towards hemorrhoids and anorectal inflammation pertain to complicated dispensing apparatus for medicinal preparations. U.S. Pat. No. 4,938,221 relates to a hemorrhoid inflammation reducing device having a hollow flexible housing that is shaped to be inserted into and removed from the anus of the rectum of a person having internal or external hemorrhoids. A coolant is disposed within the housing for shrinking the internal/external hemorrhoids. A closure is provided for sealing the coolant within the housing after the coolant is placed within the housing. U.S. Pat. No. 5,004,636 relates to a roll-type toilet tissue that is formed in three layers, with one layer having a hemorrhoid-treating medication sandwiched between the two other layers. U.S. Pat. No. 4,906,239 relates to a hemorrhoid-treatment rod that is shaped like a cone in order to dilate the anus. Ointment is forced into the cone for dispensation onto the anus, and the ointment can be massaged into the area to be treated by rotating the rod without being wiped off prematurely.

A widely used topical ointment for the treatment of hemorrhoids is PREPARATION H (a trademark of Whitehall-Robbins Healthcare located in Madison, N. J.). PREPARATION H contains active ingredients including 71.9% petrolatum, 14% mineral oil, 3% shark liver oil, and 0.25% phenylephrine HCl. Other ingredients include beeswax, benzoic acid, BHA, corn oil, glycerin, lanolin, lanolin alcohol, methylparaben, paraffin, propylparaben, thyme oil, tocopherol, and water. The phenylephrine HCl is a vasoconstrictor that is used to shrink the venous dilations which are the underlying cause of hemorrhoids.

There remains a true need for a medicament that provides enhanced relief to patients suffering from anorectal inflammation, such as the anorectal inflammation that is often associated with hemorrhoids.

Solution

The present invention overcomes the problems outlined above by providing enhanced relief to patients suffering from anorectal inflammation. This enhanced relief is obtained by using an ointment including a vasoconstrictor in combination with a penetrant-carrier of lipid soluble materials and non-sensitizing lipid-soluble antimicrobial agent. In combination, these ingredients simultaneously address the problems of venous pressure-swelling and chronic inflammation in anorectal tissues. The non-sensitizing antimicrobial active agent is effective even on patients that have been sensitized to other over-the-counter medicaments. Other distinct advantages of the preferred formulation include a relatively high melting point in excess of 100 F. to 130 F. to prevent melting of the ointment from body heat, a slightly acidic pH, and a thickness suitable for use as a protective barrier over inflamed anorectal tissues.

A topical ointment according to the invention contains a petroleum base, water, a water-soluble vasoconstrictor, and an emulsifier in an effective amount for preventing separation of the petroleum base and the water. In combination with the foregoing ingredients, the ointment contains a carrier for lipid-soluble materials and a non-sensitizing lipid-soluble antimicrobial agent.

The preferred ointment has a consistency provided by the petroleum base consisting of petrolatum in an amount less than sixty percent by weight of the ointment and the water comprising less than twenty percent by weight of the ointment. The most preferred vasoconstrictor is phenylephrine hydrochloride in an amount up to 0.3 percent by weight of the ointment. The carrier is preferably a surface-active agent, and squalene is particularly preferred. The non-sensitizing lipid-soluble antimicrobial agent is most preferably 8-hydroxyquinoline. The use of squalene in combination with 8-hydroxyquinoline and a vasoconstrictor are critical aspects of preferred embodiments of the invention that provide superior treatment results in human patients.

The ointment or cream is used by topical application to inflamed anorectal tissues. The patient usually experiences immediate soothing of pain and itching. Inflamed hemorrhoidal tissues are observed to shrink in a matter of hours, and the ointment has been used successfully to treat inflamed hemorrhoids where commercially available ointments intended for this purpose have failed.

Among soothing topical applications, in medical literature has been proposed the topical application of hyperosmotic substances in order to reduce edema through osmosis. Among these substances is also granulated sugar. Granulated sugar is used in an attempt to create a desiccant effect, as well as to create a fluid shift across the edematous hemorrhoids. The increased presence of sugar around the hemorrhoidal tissues results in this fluid shift leading to an edema reduction. This is dictated by osmotic gradients where a fluid shift is initiated, when low-concentration solvent shifts selectively into a region of higher solute concentration created by the granulated sugar placed around the protruding hemorrhoids. The preferred embodiment of the invention also includes a solution of five percent micronized sucrose as a hyperosmotic agent.

DETAILED DESCRIPTION OF THE PREFERRED EMBODIMENT

A general concept of the present invention pertains to the use of a medicament for use in the treatment of anorectal inflammation wherein the medicament includes a vasoconstrictor in combination with one or more antimicrobial agents and a carrier-penetrant for the antimicrobial agent. Action of the antimicrobial agent is facilitated by use of the carrier-penetrant.

A preferred feature of the invention is that all of the ingredients used to make the ointment have been approved for over-the-counter use, especially for use. The U.S. Food and Drug Administration has approved guidelines for the use of cosmetic chemicals that are commonly provided in over-the-counter ointments. These chemicals are submitted to the FDA for over-the-counter drug review and approval. Approval is indicated by a final publication or report in the form of a monograph. The Cosmetic Ingredient Review, Ingredient Publication Status from the Cosmetic & Toiletry Foundation Association in Washington, D.C. provides a list of approved cosmetic chemicals. This publication provides a list of approved cosmetic ingredients, the approved functions for these ingredients, and citations to the corresponding monograph publications for each ingredient. These "cosmetic" ingredients can be used in topical ointment, as well as other products such as lotion, hair dye, and the like. The general nature and function is known for each ingredient, but great variations in efficacy can be observed based upon the precise selection of ingredients and the concentration of ingredients in combination.

An emulsified petroleum base is used as a vehicle for the ointment. The petroleum base is preferably a high grade of petrolatum, such as white soft paraffin or petroleum jelly. Petrolatum is preferred for its effects in soothing the sensations of burning, itching, and pain that are experienced by those who are suffering from anorectal inflammation. The petroleum base preferably ranges from fourteen to fifteen percent by weight of the ointment. Non-petroleum waxes such as lanolin may also be added to thicken and facilitate emulsion of the base. For example, a preferred formulation contains lanolin in an amount of 2 percent of the ointment weight, in order to stabilize the emulsion.

The use of a petrolatum base in amounts less than about fifty or sixty percent of the ointment or cream by weight is significant because these amounts reflect a reduction in the amount of petrolatum that is used in comparison with other over-the-counter remedies including PREPARATION H. Users of these other ointments sometimes complain that the ointment melts and runs away from the rectal area with the effect of staining the clothes of the person who wears the ointment. The reduced weight of petrolatum in the present medicament is associated with a corresponding reduction in the effect of staining clothes if the ointment does melt; however, the ointment resists melting because it has a higher melting temperature than other ointments intended for this purpose.

Purified water is also used to form a portion of the ointment or cream base. The water solubilizes ingredients that are not soluble in the petroleum portion of the base. The amount of water preferably ranges from forty to ten percent by weight of the ointment. Preferably, no more water is added than is necessary to solubilize the water-soluble ingredients of the ointment. It is intended that the water will form a stable emulsion with the petroleum base.

Emulsifiers are used to stabilize the emulsion and provide a melting point in excess of about 100 degrees F. to 130 degrees F. A plurality of emulsifying agents are preferably used as the emulsifier. These emulsifying agents can include, by way of example, Polysorbate 60, cocoa oil, Glyceryl Monostearate as well as other conventional emulsifiers approved for cosmetic use. The emulsifiers are added in amounts that, in combination, stabilize the petroleum and water emulsion. The combined amount of emulsifier typically ranges from three to ten percent of the ointment by weight. Many of these emulsifiers have dual or triple purposes. For example, squalene functions as a surfactant and penetrant while providing a nutritional benefit to inflamed tissues.

Lanolin doubles as an emollient. Emollients are also present in preferred formulations with lanolin being the most preferred emollient. Glycerine or another humectant may be added to alternative formulations in the semisolid suppository form. In combination, the emollient and humectant portions of the ointment preferably range from sixteen to seventeen percent by weight of the ointment.

Phenylephrine hydrochloride is a vasoconstrictor that has been approved for over-the-counter use in amounts not exceeding about 0.3 of the composition weight. Phenylephrine hydrochloride is water-soluble, and preferably present in an amount equal to a 0.013:1 weight ratio of phenylephrine hydrochloride to water, not to exceed about 0.25 weight percent of phenylephrine hydrochloride in the ointment. Other vasoconstrictors may be used in the invention, but phenylephrine hydrochloride is preferred because it has been approved for use in over-the-counter ointments. The phenylephrine hydrochloride is preferably mixed with the water prior to adding the water to the petrolatum.

Sucrose is a natural hyperosmotic agent approved for cosmetic use by The Cosmetic Ingredient Review. Sucrose in the form of granulated sugar (table sugar) is a recognized medical treatment for edema reduction in cases of prolapsed hemorrhoids in supported medical studies.

The application of granulated sugar onto swollen hemorrhoids in the studies led to an immediate edema reduction and subsequent relief. After the topical application of sugar, hemorrhoids shrink, and edema is drastically reduced. Sugar absorbs the extra water by osmotically drawing out the fluid, At the same time, the area needs to be constantly covered with sugar, Gentle manual pressure on the hemorrhoids makes the procedure more efficient. The patient seemed to experience minimal pain or discomfort during the operation. After 10 minutes of application, the difference is noticeable with the naked eye. The protruding hemorrhoids gradually become significantly smaller. Eventually, the prolapsed hemorrhoid is easily reduced back into the anal canal. This treatment does not apply in thrombosed external hemorrhoids due to the fact that the skin that covers external hemorrhoids inhibits the water shifting effect of sugar.

Low sensitizing preservatives are useful for enhancing the shelf storage life of the ointment. It is preferred to avoid the use of chlorides as preservatives because chlorides can sometimes promote severe sensitization reactions in patients with side effects that include enhanced inflammation, ulceration, and bleeding. Tocopherol acetate is useful as a preservative and has the additional benefit of providing nutritional benefit to inflamed anorectal tissues in the form of a vitamin E derivative.

The sensitizing antimicrobial agent is preferably a lipid soluble material. A particularly preferred cosmetic biocide for use in the present invention as an antimicrobial agent is Potassium sorbate. The antimicrobial agent is preferably not a chloride because chlorides are likely to induce sensitivity reactions that sometimes can produce escharotic effects. The use of Potassium Sorbate is further preferred for the effect of providing a slightly acidic pH to the overall ointment or cream. The acidic pH promotes healing of inflamed anorectal tissues.

The following non-limiting examples are used to present the most preferred product formulation, as well as evidence of biological utility of this formulation in actual use on human patients.

Example 1

Topical Ointment for Use in the Treatment of Anorectal Inflammation

The following ingredients were weighed out and blended to substantial homogeneity in a stable emulsion to form a medicinal cream. This formulation is particularly preferred for its ability to adhere to inflamed anorectal tissues while providing multiple benefits to the tissues according to the principles discussed above.

TABLE 1

| Sr. No. | Raw Material | Weight Percent | Purpose |
|---|---|---|---|
| 1 | Phenylephrine HCl | 0.25 | Active ingredient vasoconstrictor |
| 2 | Sucrose Micronized | 5 | active ingredient hyperosmotic, mild desiccant |
| 3 | Theobroma Oil (Cocoa) | 3 | Emulsifier, thickening agent |
| 4 | White Soft Paraffin | 14 | active agent for soothing and protection of inflamed tissues |
| 5 | Polysorbate 60 | 2 | emulsifier |
| 6 | Cetyl Alcohol | 4 | moisturizer |
| 7 | Glyceryl Monostearate | 2 | emulsifier |
| 8 | Lanolin Hydrogenated | 2 | Emulsifier, protectant |
| 9 | Glycerin | 20 | preservative |
| 10 | Butylated Hydroxy Anisole | 0.005 | Antioxidant and preservative |
| 11 | dl-alpha-Tocopherol | 0.01 | Antioxidant and preservative |
| 12 | Potassium Sorbate | 0.2 | antimicrobial agent, preservative |
| 13 | Purified Water | 47.535 | Solubilizing agent for Phenylephrine HCl, thinner |

Example 2

Use of the Ointment on Humans

The main base of the cream conforms to the Part 346 FDA approved monograph for anorectal over-the-counter treatments and is generally recognized as safe and effective when used to relieve symptoms caused by anorectal disorders in the anal canal, perianal area, and/or the lower rectal areas in which Phenylephrine hydrochloride 0.25 percent is the active vasoconstrictor ingredient.

The addition of hydrolyzed sucrose as a hyperosmotic is based on medical studies wherein the application of granulated sugar onto swollen hemorrhoids resulted in immediate edema reduction and subsequent relief. Sucrose is a disaccharide made up of glucose and fructose. This ingredient has been recognized as generally safe and effective food additives by the FDA, and its dermal effects have been analyzed by the Cosmetic Ingredient Review, which concluded its use as safe in cosmetics as a skin conditioning agent.

Those skilled in the art will understand that the preferred embodiments described above may be subjected to apparent modifications without departing from the true scope and spirit of the invention. The inventors, accordingly, hereby state their intention to rely upon the Doctrine of Equivalents, in order to protect their full rights in the invention.

The invention claimed is:

1. A topical medicament for treating anorectal inflammation comprising:
    a petroleum base;
    water;
    phenylephrine hydrochloride;
    an emulsifier in a quantity effective for maintaining a homogeneous mixture of the petroleum base and the water;
    a carrier suitable for lipid-soluble materials;
    glycerin;
    cocoa butter;
    micronized sucrose; and
    a compatible material selected from the group consisting of tocopherol acetate, methyl salicylate, parabens, EDTA, methyl tocopherol and combinations thereof.

2. The topical medicament of claim 1, wherein the petroleum base comprises petrolatum in a concentration not exceeding fifteen percent by weight relative to the total weight of the medicament.

3. The topical medicament of claim 2, wherein the phenylephrine hydrochloride is present in a concentration not exceeding 0.25 percent by weight relative to the total weight of the medicament.

4. The topical medicament of claim 3, wherein the water comprises less than fifty percent by weight of the total weight of the medicament.

5. The topical medicament of claim 1, wherein the carrier for lipid-soluble materials is a surface-active agent, comprising polysorbate.

6. The topical medicament of claim 1, wherein the compatible material is methyl tocopherol.

7. A method for treating anorectal inflammation, the method comprising:
    providing a medicament that includes a petroleum base, water, phenylephrine hydrochloride, an emulsifier in an effective amount to prevent separation of the petroleum base and the water, a carrier for lipid-soluble materials, glycerin, cocoa butter, micronized sucrose; and a compatible material selected from the group consisting of tocopherol acetate, methyl salicylate, paragons, EDTA, and combinations thereof;
    applying the medicament to inflamed anorectal tissues; and
    allowing the medicament to act on the tissues to alleviate symptoms of inflammation.

* * * * *